(12) United States Patent
Nielsen et al.

(10) Patent No.: US 8,896,292 B2
(45) Date of Patent: Nov. 25, 2014

(54) SYSTEM AND METHOD FOR GAIN ADJUSTMENT IN TRANSIMPEDANCE AMPLIFIER CONFIGURATIONS FOR ANALYTE MEASUREMENT

(75) Inventors: Jakob Nielsen, Waterloo (CA); Dustin Griesdorf, Waterloo (CA)

(73) Assignee: Semiconductor Components Industries, LLC, Phoenix, AZ (US)

( * ) Notice: Subject to any disclaimer, the term of this patent is extended or adjusted under 35 U.S.C. 154(b) by 312 days.

(21) Appl. No.: 13/334,631

(22) Filed: Dec. 22, 2011

(65) Prior Publication Data

US 2013/0162240 A1   Jun. 27, 2013

(51) Int. Cl.
  *G01R 19/00* (2006.01)
  *H03G 3/00* (2006.01)

(52) U.S. Cl.
  USPC ............................. 324/123 R; 330/278

(58) Field of Classification Search
  CPC .......... H03F 3/45475; H03F 2200/261; H03F 2203/45528; H03F 2203/45536; H03G 1/0088; G01N 27/3273
  See application file for complete search history.

(56) References Cited

U.S. PATENT DOCUMENTS

| | | | |
|---|---|---|---|
| 4,559,241 A | 12/1985 | Obitsu et al. | |
| 6,693,498 B1 | 2/2004 | Sasabata et al. | |
| 6,908,535 B2 | 6/2005 | Rankin et al. | |
| 7,090,764 B2 | 8/2006 | Iyengar et al. | |
| 7,407,811 B2 | 8/2008 | Burke et al. | |
| 2009/0027040 A1 | 1/2009 | Kermani et al. | |
| 2010/0259397 A1* | 10/2010 | Du et al. | 340/618 |
| 2012/0235739 A1* | 9/2012 | Griesdorf et al. | 330/129 |

* cited by examiner

*Primary Examiner* — Minh N Tang
(74) *Attorney, Agent, or Firm* — Rennie William Dover

(57) ABSTRACT

A system and method for analyte measurement is provided. The system includes: a transimpedance amplifier including: at least one operational amplifier including a first input coupling to a reference voltage, a second input coupling to a sensor for sensing the analyte, and an output; and at least one passive circuit element having a first terminal and a second terminal, the first terminal of the at least one passive circuit element coupling to the second input of the at least one operational amplifier, and a circuit for adjusting a gain of the transimpedance amplifier for the measurement of the analyte. The method includes: monitoring a level of the output of the at least one operational amplifier for the measurement of the analyte; and adjusting a gain of the transimpedance amplifier during the measurement of the analyte.

20 Claims, 7 Drawing Sheets

the appended drawings wherein:

SYSTEM AND METHOD FOR GAIN ADJUSTMENT IN TRANSIMPEDANCE AMPLIFIER CONFIGURATIONS FOR ANALYTE MEASUREMENT

FIELD OF INVENTION

The present invention relates to a system and method for signal processing, and more specifically to a system and method for gain adjustment in a transimpedance amplifier configuration for analyte measurement.

BACKGROUND OF THE INVENTION

A blood glucose meter is used by individuals to measure the concentration of glucose in their blood. People with diabetes have a special interest in measuring the concentration of glucose as the level of glucose can be an indication of whether treatment of their diabetes is required or not.

Handheld, commercially available blood glucose meters are typically used for this purpose. Such commercially available meters work by having the patient place a small blood drop on a test strip (a "sensor"). Then the test strip is inserted in a glucose meter followed by processing of the test strip in the glucose meter to determine the concentration of the glucose.

In typical operation, the sensor will produce a small current (known as "work current") when biased with a voltage. The current will vary as function of the chemical reaction happening in the test strip. This variation can have a very large dynamic range, leading to a possible saturation on the output of the sensor interface. Therefore there is a need to adjust the operation of the electro-chemical sensor interface to accommodate such large variations in work currents without the sensor interface saturating.

SUMMARY OF THE INVENTION

It is an object of the invention to provide a method and system that obviates or mitigates at least one of the disadvantages of existing systems.

According to one aspect of the disclosure there is provided a system for analyte measurement, which includes: a transimpedance amplifier including: at least one operational amplifier including a first input coupling to a reference voltage, a second input coupling to a sensor for sensing the analyte, and an output; and at least one passive circuit element having a first terminal and a second terminal, the first terminal of the at least one passive circuit element coupling to the second input of the at least one operational amplifier, and a circuit for adjusting a gain of the transimpedance amplifier for the measurement of the analyte.

According to another aspect of the disclosure there is provided a method for analyte measurement in use of a transimpedance amplifier where the transimpedance amplifier includes at least one operational amplifier including a first input coupling to a reference voltage, a second input coupling to a sensor for sensing the analyte, and an output, the method including: monitoring a level of the output of the at least one operational amplifier during the measurement of the analyte; and based on the level of the output of the at least one operational amplifier, adjusting a gain of the transimpedance amplifier for the measurement of the analyte.

BRIEF DESCRIPTION OF THE DRAWINGS

These and other features of the invention will become more apparent from the following description in which reference is made to the appended drawings wherein.

DETAILED DESCRIPTION

Figure 1:
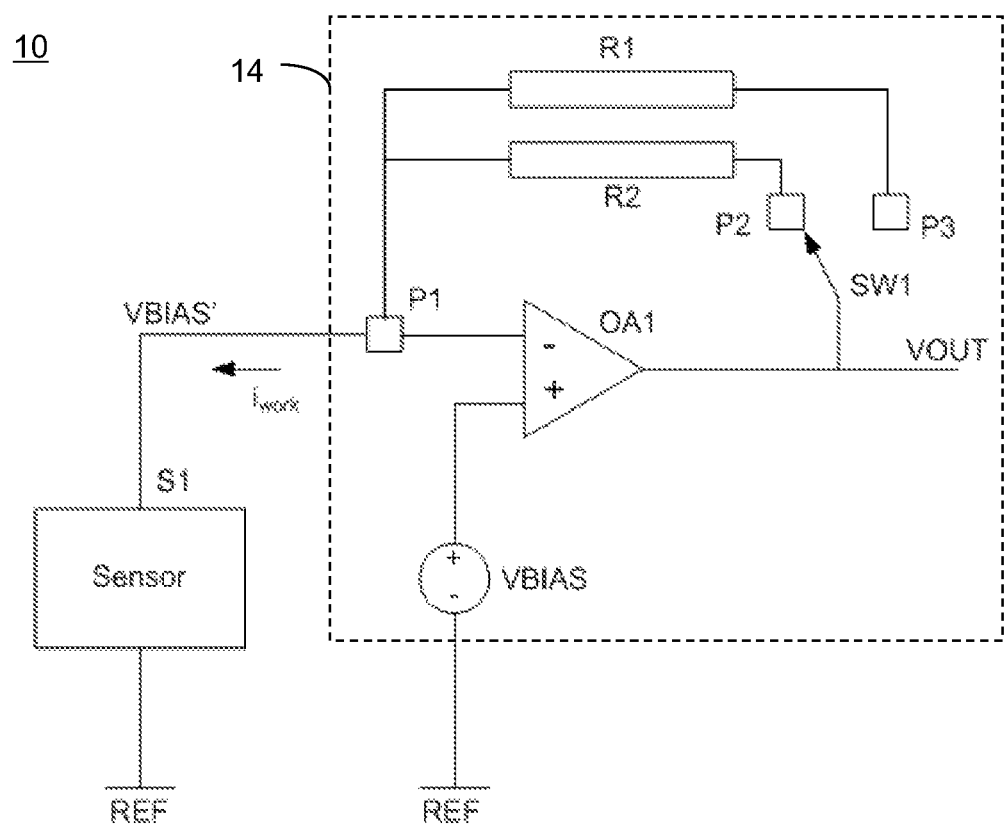
FIG. 1 is a diagram illustrating a measurement system having a sensor and a sensor interface for the sensor where the sensor interface is in a first mode.

The embodiments are described in detail using a meter for measuring analyte, such as a glucose meter for measuring the concentration of glucose in blood; however, this does not exclude the possibility of measuring the level of any other analyte. It would be appreciated by one of ordinary skill in the art that the term "analyte" represents, without limitation, to a substance or chemical constituent in a physiological fluid, such as blood, urine, spinal fluid, lymph fluid, which can be analyzed.

Referring to FIGS. 1-4, there are illustrated an example of a measurement system 10 including an electro-chemical sensor S1 and a processing engine 12 having an electro-chemical sensor interface 14. The sensor interface 14 operatively couples to the sensor S1 to interfere with the measurement of an analyte of interest in the sensor S1. In this example, the processing engine 12 forms a glucose meter measurement system. The sensor S1 produces a work current $i_{work}$ associating with the concentration of glucose. As described below, the sensor interface 14 is adjustable to accommodate large variations of work currents for any sensors attached to the sensor interface 14.

The processing engine 12 includes a controller 16 for controlling the measurement of glucose concentration level where the controller 16 couples to the output VOUT of the sensor interface 14 and processes the output VOUT. The controller 16 operatively coupling to the output of the sensor interface 14 monitors the size of the work current $i_{work}$ associating with the concentration of glucose as it is being sampled. The sensor S1 may also operatively couple to the controller 16. The controller 16 may be any microcontroller or digital signal processor, internal or external, suitable for the purpose.

It would be appreciated by one of ordinary skill in the art that other components not shown in FIGS. 1-4 may exist in the system 10. Other components such as one or more A/D converters, more operational amplifiers, reference voltages, battery components may exist in the system 10 or the sensor interface 14. The output VOUT may be sampled in an analog-to-digital converter (ADC) before it enters the controller 16. The ADC for sampling the output VOUT may be included in the controller 16. The processing engine 12 may be in a handheld device for glucose measurement, and the sensor S1 may form a test strip so as to detachably couple to the sensor interface 14. The system 10 may assess the glucose level in a drop of blood placed on the sensor S1.

Typically the sensor S1 is connected between a bias voltage VBIAS' and a reference voltage REF. The reference voltage REF may be, for example, but not limited to, GND (ground).

The sensor interface 14 includes a transimpedance amplifier for converting a current generated by a chemical reaction on the sensor S1 into a voltage. The transimpedance amplifier in the sensor interface 14 includes one or more than one operational amplifiers (opamp) OA1 and one or more passive circuit elements. In FIGS. 1-4, one opamp OA1 is shown by way of example. The opamp OA1 may be selected so that it has characteristics suitable for the purpose of measuring work currents. The opamp OA1 has a certain output dynamic range. Within the dynamic range, the opamp OA1 converts the work current $i_{work}$, for example, to a voltage that is proportional to the work current $i_{work}$.

The opamp OA1 has a negative input terminal (or negative input) P1, a positive input terminal (or a positive input) and an output terminal (or an output). In this example, VOUT may be used to represent the output of the sensor interface 14 or the output (terminal) of the opamp OA1. A bias voltage VBIAS is applied to the positive terminal of the opamp OA1. The voltage VBIAS is typically generated by a reference voltage circuit or a derivative thereof, which includes a reference voltage supply REF. In one example, the bias voltage VBIAS is substantially equal to VBIAS'. The opamp OA1 is operatively coupled to power supply rails (upper and lower rails). The upper rail may be, for example, but not limited to, a positive supply voltage, and the lower rail may be, for example, but not limited to, connected to ground. The upper rail may be substantially equal to the positive opamp supply voltage and the lower rail may be substantially equal to the negative opamp supply voltage. The output dynamic range of the opamp OA1 may be primarily dominated by the opamp supply voltages or the upper rail and the lower rail. Other factors may also impact the output dynamic range of the opamp OA1.

The sensor interface 14 includes a switch SW1 for adjusting (or switching) a gain of the transimpedance amplifier. The switch SW1 is placed on the output VOUT of the opamp OA1. In this example, one terminal of the switch SW1 is operatively connected to VOUT that is operatively coupled to the input of the controller 16, regardless of its switching condition (e.g., on/off). Another terminal of the switch SW1 is connectable to terminal P2 and/or P3.

The gain of the transimpedance amplifier is adjustable by operating on the switch SW1, resulting in avoidance of the opamp output VOUT saturation during the blood glucose measurement. Further, the gain may be switchable without temporarily bringing the opamp OA1 into an unstable configuration during the actual switch.

The switch SW1 and the transimpedance amplifier (or the opamp OA1) may be integrated on one chip or connected externally. The sensor interface 14 may be a chip and P1, P2 and P3 may be external electrodes.

In FIGS. 1-4, two passive circuit elements R1 and R2 are shown by way of example. The passive circuit element R1 is connected between the negative input terminal P1 of the opamp OA1 and the terminal P3 that is connectable to the switch SW1. The passive circuit element R2 is connected between the negative input P1 of the opamp OA1 and the terminal P2 that is connectable to the switch SW1. The passive circuit elements R1 and R2 are, for example, resistors.

It would be appreciated by one of ordinary skill in the art that the sensor interface 14 may include one or more passive circuit elements, wherein in embodiments with two or more passive circuit elements, the two or more passive circuit elements are configured in parallel to one opamp. It would be appreciated by one of ordinary skill in the art that the passive circuit elements operatively connectable to the switch SW1 are not limited to the resistors, and may be other elements, such as capacitors or memristors or combinations of resistors and capacitors and memristors. It would be appreciated by one of ordinary skill in the art that the passive circuit element operatively connectable to the switch SW1, e.g., R2, may be an active circuit element emulating a passive circuit element.

The switch SW1 is connectable to the passive circuit elements R1 and R2 at terminals P3 and P2, respectively (see FIGS. 1-4). Based on the connection to P2 and P3, the switch SW1 allows for a plurality of modes of operations. The controller 16 may determine the operation mode based on, for example, VOUT or a work current $i_{work}$.

The switch SW1 connects the output VOUT of the opamp OA1 in either of the following ways:
VOUT=P2 (see FIG. 1: one mode)
VOUT=P3 (see FIG. 2: another mode)
VOUT=P2 and P3 (see FIG. 3: a further mode)

In a further example, there may be a mode where the switch SW1 is open so that VOUT is not coupled to P2 and P3.

Given the settings of the switch SW1 outlined above the following combinations of the circuit elements can exist between the negative input terminal P1 of OA1 and the output VOUT of OA1:
P1 coupling to VOUT via R1 only (see FIG. 2)
P1 coupling to VOUT via R2 only (see FIG. 1)
P1 coupling to VOUT via R1 and R2 (see FIG. 3)
In a further example, the switch SW1 may be open so that neither R1 nor R2 forms a connection between P1 and VOUT.

The work current $i_{work}$ runs through the sensor S1. Depending on the setting of the switch SW1, the work current $i_{work}$ will also run through R1, R2 or both of R1 and R2. Thus, depending on the setting of the switch SW1, the input to the opamp OA1 and VOUT will change.

In FIGS. 1-4, the switch SW1 is placed on the output VOUT of the opamp OA1, rather than putting it on the negative input terminal P1 of the opamp OA1. Thus any leakage current in the switch SW1 will not impact the work current $i_{work}$. If the switch SW1 had been placed on the input terminal of the opamp OA1, some of the work current could potentially go through the switch leakage path to GND rather than through the sensor S1 causing an inaccuracy in the glucose measurement.

Further, the switch SW1 is placed on the output VOUT of the opamp OA1, and thus the switch SW1 gets driven through a low-impedance (typical for an opamp) so the transient response of the switch SW1 will not be impacted by the capacitance of the switch.

In the case where the circuit elements R1 and R2 are resistors, the work current flow will result in a voltage at VOUT. In the description below, "R1" and "R2" represents resistors, and "VOUT" represents the voltage at the output of the opamp OA1. The magnitude of the voltage VOUT depends on the values of R1 and/or R2. The resistor values may be referred to as the gain values as they "amplify" a small current $i_{work}$ into the voltage VOUT.

The output dynamic range of an opamp is primarily dominated by the opamp supply voltages (upper and lower rail). Typically the upper rail would be substantially equal to the positive opamp supply voltage and the lower rail would be substantially equal to the negative opamp supply voltage. Other factors may also impact the output dynamic range of the opamp.

When determining the concentration of an analyte, the dynamic range of the work current can range from very small to very large. Small work currents can be in the order of a few hundred pA ($i_{work,low}$) whereas large work currents can be in the order of several hundred uA ($i_{work,high}$). If the work current is coupled to an opamp, this dynamic range of the work current is mapped into the output dynamic range of the opamp. Therefore the following constraints may exist for this mapping:

1) No opamp operation close to or above the upper rail of the opamp power supply.

2) No opamp operation close to or below the lower rail of the opamp power supply.

Operating above the upper rail of the opamp power supply or operating below the lower rail of the opamp power supply may result in saturation of the VOUT voltage. By contrast, the transimpedance amplifier of FIGS. 1-4 will be able to accept a wider range of work currents than that of OA1, thereby having a gain larger than that of OA1.

Embodiment 1

In one embodiment, it is assumed that the element R2 is a resistor of larger value than the value of the resistor R1. Work current $i_{work}$ may be in the range of, for example, hundreds of pA to hundreds of uA.

For work currents $i_{work}$ that are small in the range the voltage VOUT would be generated by forcing the work current through the large resistor R2 by setting the switch SW1 to point to the terminal P2 as shown in FIG. 1.

Figure 3:
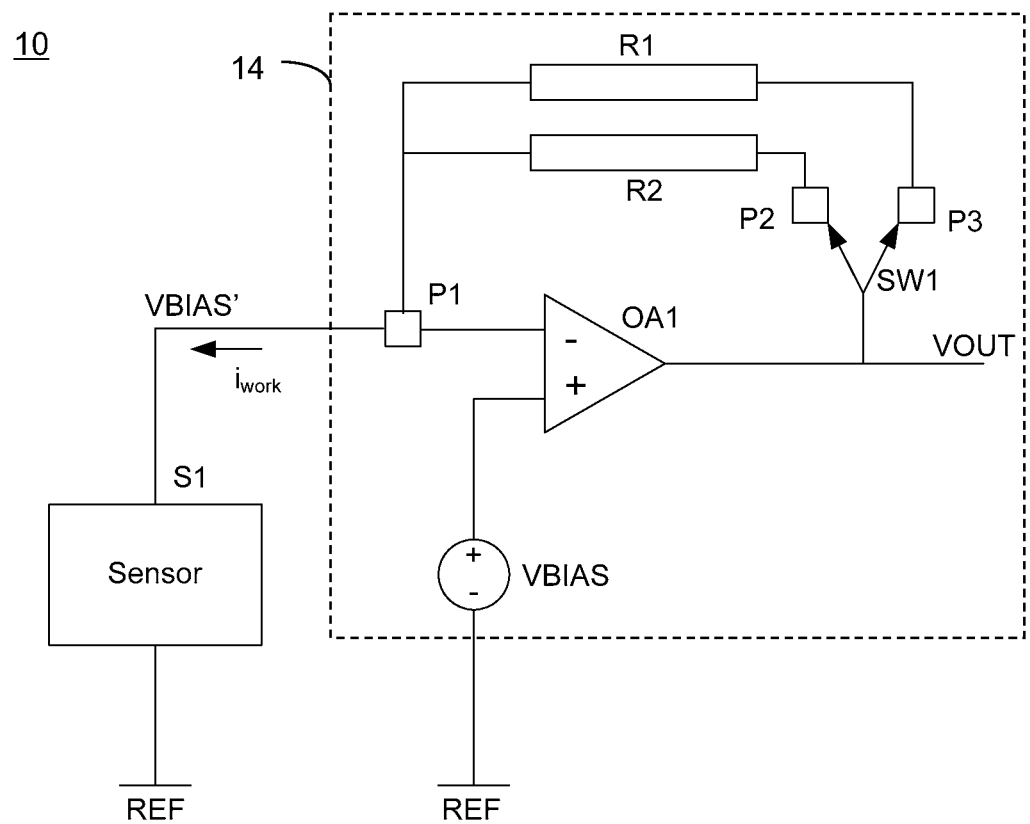
FIG. 3 is a diagram illustrating the system of FIG. 1 where the sensor interface is in a third mode.

For work currents $i_{work}$ that are large in the range the voltage VOUT would be generated by forcing the work current through the resistor R1 in parallel with the resistor R2 by setting the switch SW1 to point to the terminals P2 and P3 simultaneously, as shown in FIG. 3.

Figure 2:
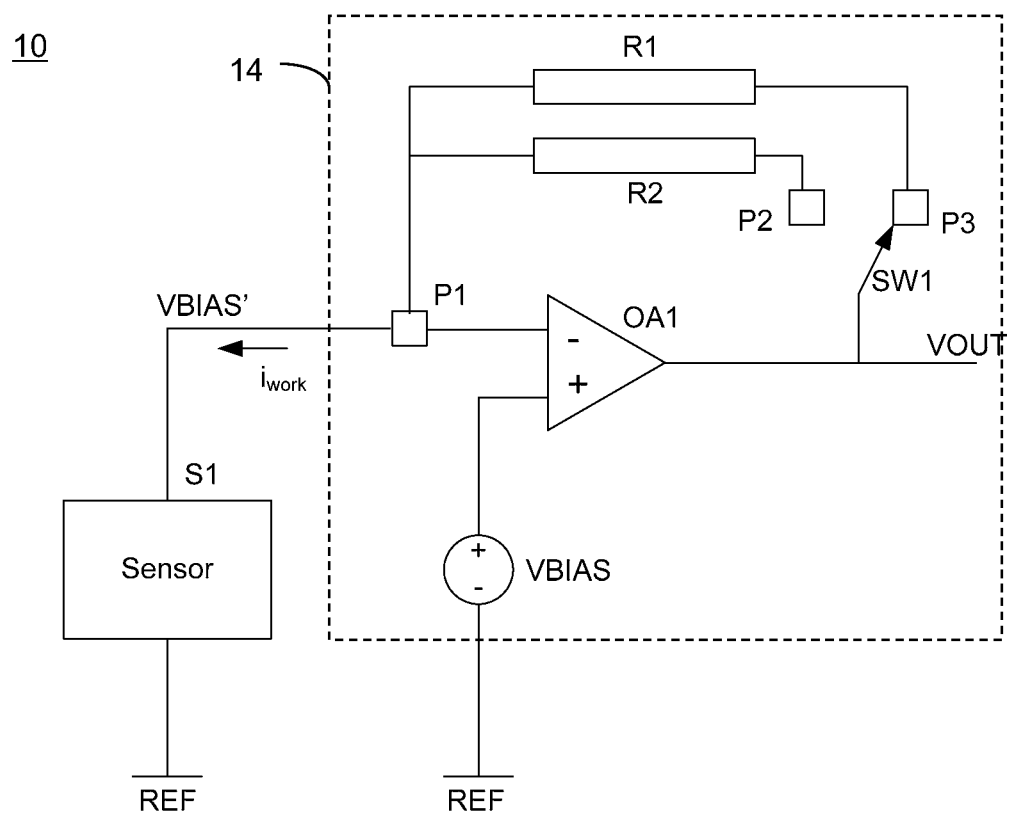
FIG. 2 is a diagram illustrating the system of FIG. 1 where the sensor interface is in a second mode.

For work currents $i_{work}$ that are in between the small and the large current outlined above, the voltage VOUT would be generated by forcing the work current $i_{work}$ through the small resistor R1 by setting the switch SW1 to point to the terminal P3, as shown in FIG. 2.

Embodiment 2

In another embodiment, only the small and the large work currents apply. The element R2 may be a resistor of larger value than the value of the resistor R1. In this embodiment the switch SW1 would connect the terminal P2 to the output VOUT when having a small work current, as shown in FIG. 1. Further, the switch SW1 would connect the terminal P3 to the output VOUT when having a large work current, as shown in FIG. 2.

Although only two ranges are desired in this case it is still advantageous to have a further mode for the switch SW1 where it connects both of the terminals P2 and P3 to the output VOUT, as shown in FIG. 3. The reason for connecting both of the terminals P2 and P3 to the output VOUT is when switching from the terminal P2 to the terminal P3 there could be a small switching delay. This delay could result in momentarily open-loop operation of the opamp OA1 and a resulting instability in the operation of the opamp OA1.

Open-loop operation may not be desired when performing analyte measurements. By having the mode where the terminals P2 and P3 both connect to VOUT the switching from one terminal (e.g., P2) to another terminal (e.g., P3) may happen as follows:

1) First connect the terminal P2 to the output VOUT.

2) Leave P2 connected to VOUT and connect the terminal P3 to the output VOUT.

3) Remove connection between the terminal P2 and the output VOUT.

By performing the switching this way there is no point in the switching process where the opamp OA1 operates in an open-loop condition.

Embodiment 3

In a further embodiment, the resistor R1 is a very large resistor (e.g., Mohm range), and the resistor R2 is a smaller resistor (e.g., less than Mohm range). The switch SW1 initially connects to the large resistor R1 via the terminal P3. The switch SW1 would connect to the small resistor R2.

This operation may be desired in variations of the blood glucose meter application where the opamp OA1 is used to detect the presence of an analyte on the test strip that is inserted into the glucose meter. In this case the presence of the analyte would result in very low work current that would cause the output VOUT from the opamp OA1 to transition from its lower rail to its upper rail. This transition of VOUT from the lower rail to the upper rail can be used as trigger for the controller 16. Once the presence of the analyte has been detected the application may switch to operate with the smaller resistor R2.

Figure 4:
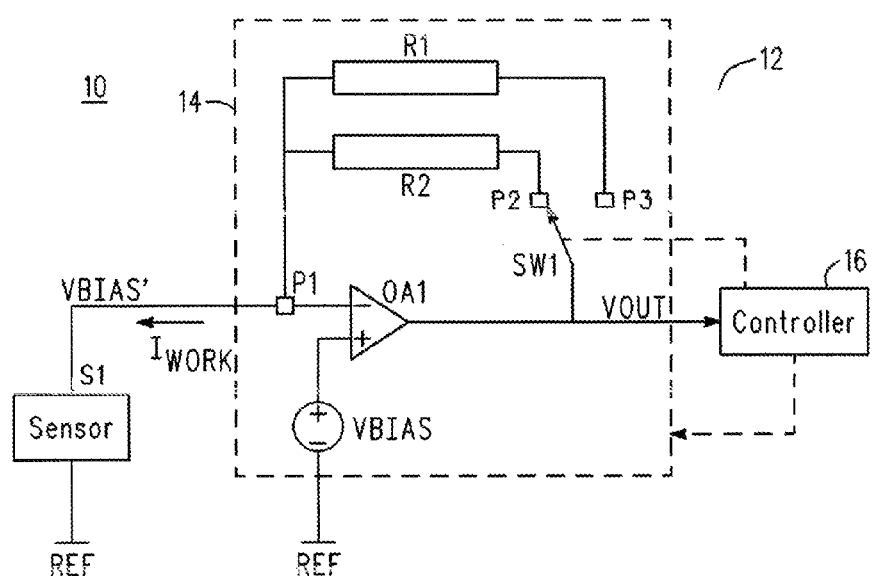
FIG. 4 is a diagram illustrating the system of FIG. 1 together with a controller where an output of the sensor interface is operatively coupled to the controller.
Figure 5:
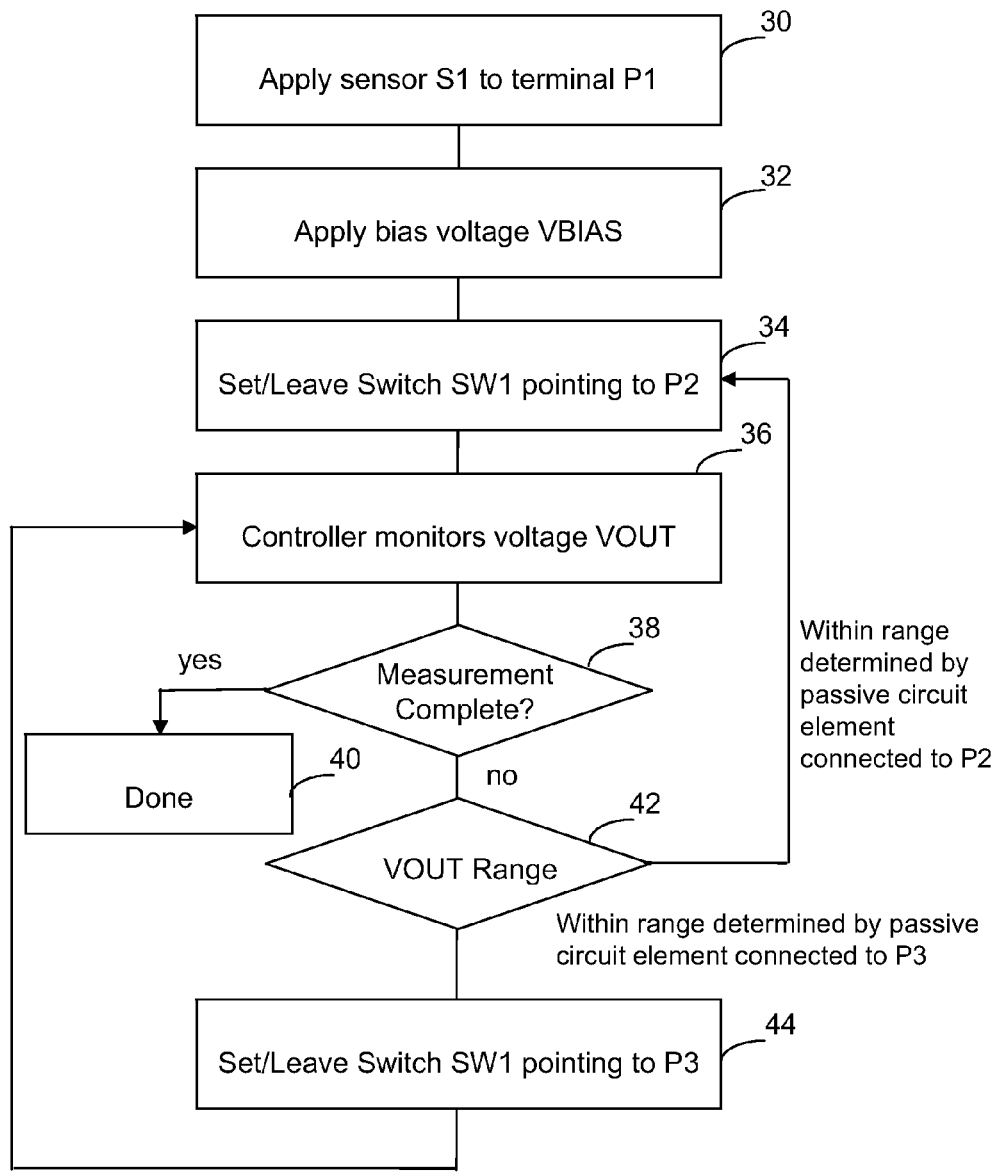
FIG. 5 is a flow chart illustrating one example of an operation flow associated with the system of FIGS. 1-4.

Referring to FIGS. 1, 4 and 5, the system 10 may operate as follows: The sensor S1 is applied to the terminal P1 (step 30), and then the bias voltage VBIAS is applied to the sensor interface 14 (step 32). The system 10 sets/leaves the switch SW1 pointing to, for example, the terminal P2 (step 34). The controller 16 monitors the output voltage VOUT (step 36). It is determined that the measurement is completed (step 38). If yes at step 38, the measurement operation is over (step 40), and the measurement result may be provided to a user via, for example, a visual signal, an audio signal or a printed signal. If no at step 38, VOUT level is determined (step 42). If VOUT is within the range determined by a passive circuit element connected to the terminal P2 (i.e., R2 in FIGS. 1 and 4), the operation goes back to step 34 and VOUT is further monitored at step 36. If VOUT is within the range determined by a passive circuit element connected to the terminal P3 (i.e., R1 in FIGS. 1 and 4), the system 10 sets/leaves the switch SW1 pointing to the terminal P3 (step 44). After step 44, the operation goes back to step 36 where VOUT is further monitored by the controller 16.

In this case, the switch SW1 is selectively coupled to the terminal P2 or P3 based on VOUT until the measurement is completed. The measurement may be completed when the output VOUT of the sensor interface 14 reaches a predetermined threshold and/or becomes stable within a predetermined range.

Figure 6:
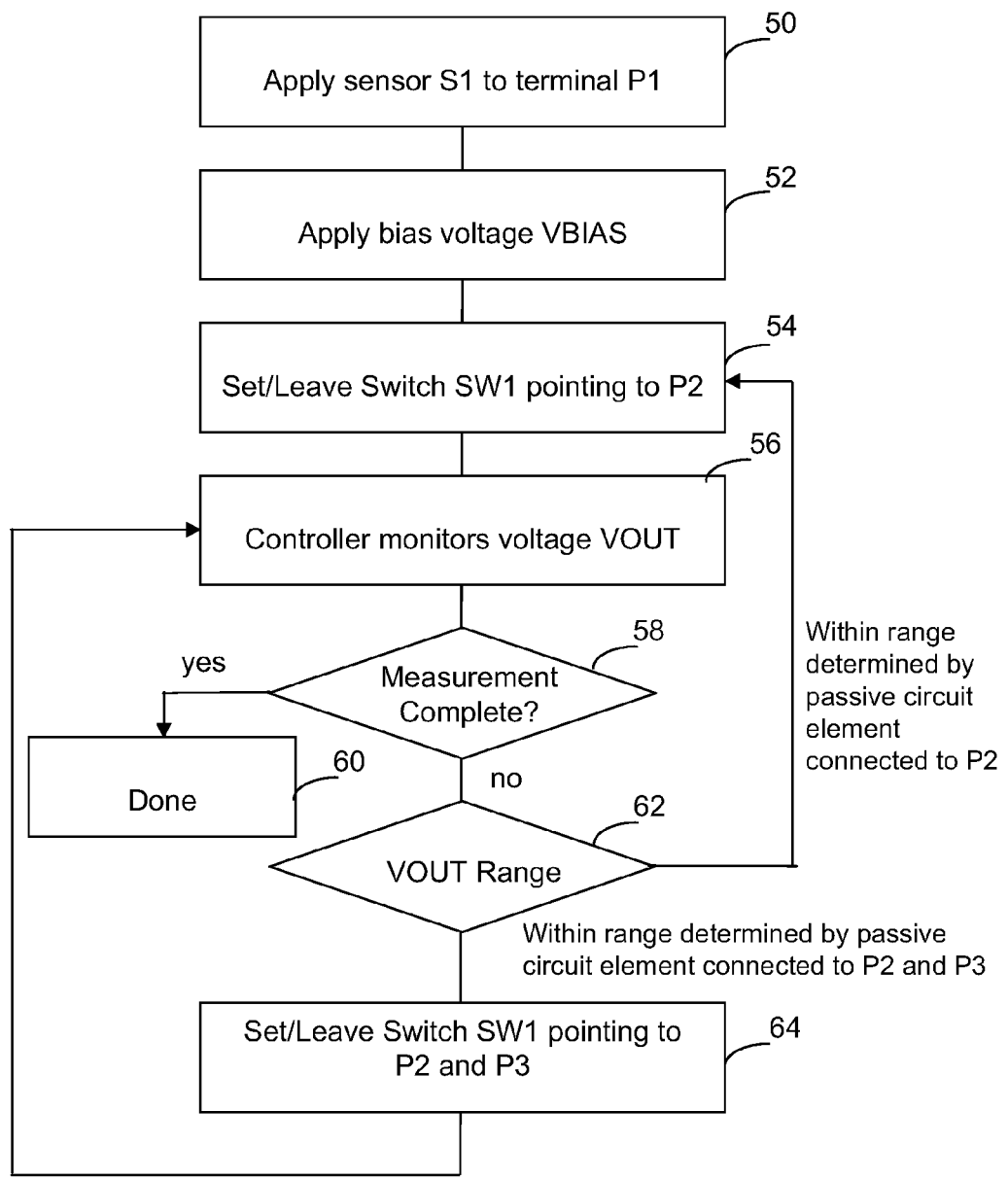
FIG. 6 is a flow chart illustrating another example of an operation flow associated with the system of FIGS. 1-4.

Referring to FIGS. 1, 4 and 6, the system 10 may operate as follows: The sensor S1 is applied to the terminal P1 (step 50), and then the bias voltage VBIAS is applied to the sensor interface 14 (step 52). The system 10 sets/leaves the switch SW1 pointing to, for example, the terminal P2 (step 54). The controller 16 monitors the output voltage VOUT (step 56). It is determined that the measurement is completed (step 58). If yes at step 58, the measurement operation is over (step 60), and the measurement result may be provided to a user via, for example, a visual signal, an audio signal or a printed signal. If no at step 58, VOUT level is determined (step 62). If VOUT is within the range determined by a passive circuit element connected to the terminal P2 (i.e., R2 in FIGS. 1 and 4), the operation goes back to step 54 and VOUT is further monitored at step 56. If VOUT is within the range determined by passive circuit elements connected to the terminals P2 and P3 (i.e., R2 and R1 in FIGS. 1 and 4), the system 10 sets/leaves the switch SW1 pointing to P2 and P3 (step 64). After step 64, the operation goes back to step 56 where VOUT is further monitored by the controller 16.

In this case, the switch SW1 is selectively coupled to the terminal P2 or both of the terminals P2 and P3 based on VOUT until the measurement is completed.

Figure 7:
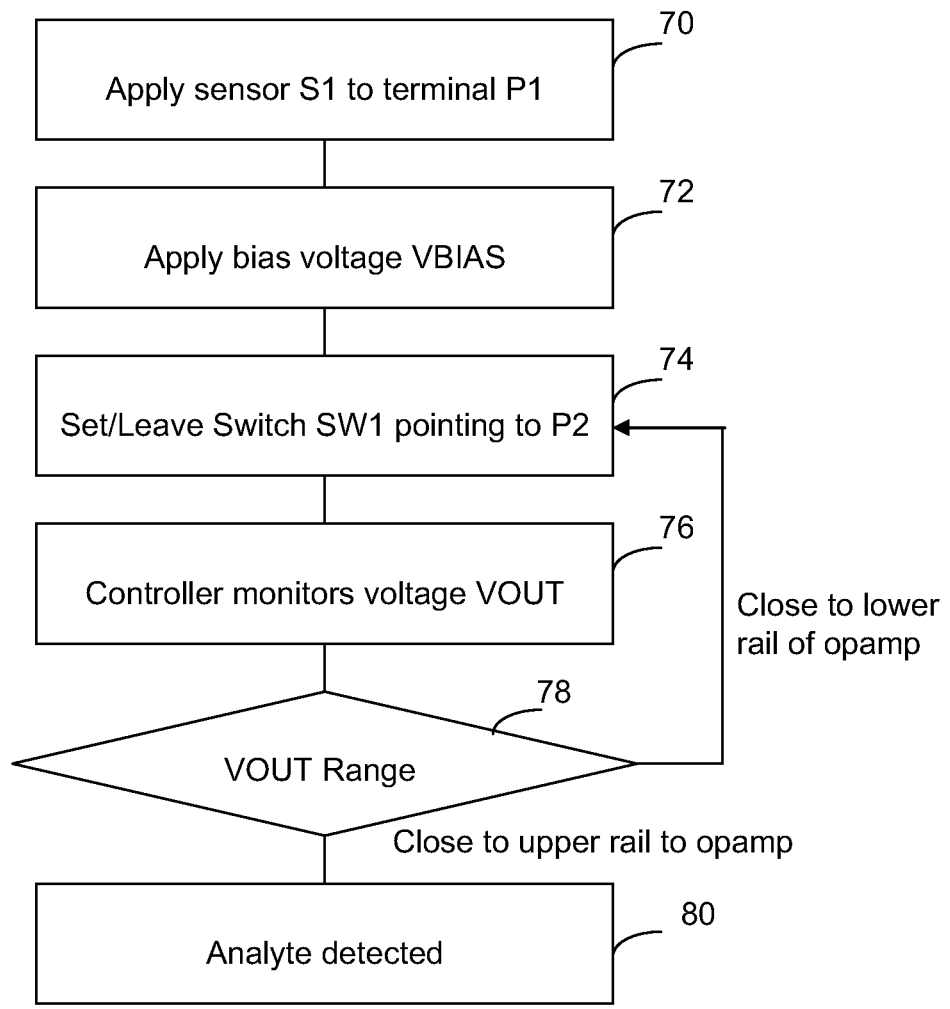
FIG. 7 is a flow chart illustrating a further example of an operation flow associated with the system of FIGS. 1-4.

Referring to FIGS. 1, 4 and 7, the system 10 may operate as follows: The sensor S1 is applied to the terminal P1 (step 70), and then the bias voltage VBIAS is applied to the sensor interface 14 (step 72). The system 10 sets/leaves the switch SW1 pointing to, for example, the terminal P2 (step 74). The controller 16 monitors the output voltage VOUT (step 76). The range of VOUT is determined (step 78). If VOUT is close to or substantially at the lower rail for the opamp OA1, the operation goes back to step 74 and the switch SW1 is operated, and VOUT is further monitored by the controller 16 (step 78). If VOUT is close to or substantially at the upper rail for the opamp OA1, this is used as a trigger for the controller 16 so that it detects the analyte (step 80).

In this case, the switch SW1 is selectively coupled to the terminal P2 based on VOUT until the measurement is done.

According to the embodiments, the gain of the transimpedance amplifier's opamp can be adjusted (switched) to match the large dynamic range of the current produced by the chemical reaction in the sensor. The gain switching can be done without creating an open-loop configuration of the opamp so that temporary open-loop operation of the transimpedance amplifier's opamp is avoided. Furthermore, the gain range can vary by selecting transimpedance amplifier's feed-back resistors. By disposing the switch SW1 to the opamp's output, it can avoid switch leakage currents impacting the glucose measurement.

The opamp system can be configured with three external terminals (P1, P2, P3 of FIGS. 1-4) as opposed to the case where the switch would be located on the negative input terminal of the opamp and a total of four external terminals would be required to monitor all opamp connections.

One or more currently preferred embodiments have been described by way of example. It will be apparent to persons skilled in the art that a number of variations and modifications can be made without departing from the scope of the invention as defined in the claims.

What is claimed is:

1. A system for analyte measurement, comprising:
    a transimpedance amplifier including:
        at least one operational amplifier including a first input coupling to a reference voltage, a second input coupling to a sensor for sensing the analyte, and an output;
        at least one passive circuit element having a first terminal and a second terminal, the first terminal of the at least one passive circuit element coupling to the second input of the at least one operational amplifier; and
    a circuit for adjusting a gain of the transimpedance amplifier for the measurement of the analyte, the circuit for adjusting the gain of the transimpedance amplifier directly connected to the output of the transimpedance amplifier and configured to change the coupling with the at least one passive circuit element without open-loop operation of the at least one operational amplifier.

2. A system as claimed in claim 1, wherein the circuit comprises:
    a switch for connecting or disconnecting both of the output of the at least one operational amplifier and an input for a controller for detecting and/or measuring the analyte level, to or from the second terminal of the at least one passive circuit element.

3. A system as claimed in claim 2, wherein the output of the at least one operational amplifier is operatively coupled to the input for the controller, regardless of the switching condition of the switch.

4. A system as defined in claim 2, wherein the circuit comprises:
    a module for controlling the switch based on a current running through the sensor.

5. A system as defined in claim 2, wherein the switch and the operational amplifier are integrated on a chip or connected externally.

6. A system as claimed in claim 1, wherein the at least one passive circuit element comprises:
    a plurality of passive circuit elements disposed in parallel, the first terminal of each passive circuit element connecting to the second input of the at least one operational amplifier, the second terminal of each passive circuit element being connectable to the output of the at least one operational amplifier and an input for a controller for detecting and/or measuring the analyte level.

7. A system as claimed in claim 6, wherein the circuit comprises:
    a switch including:
        a first terminal connecting both of the output of the at least one operational amplifier and the input for the controller, and
        a second terminal connecting or disconnecting to or from the second terminal of at least one of the plurality of passive circuit elements.

8. A system as claimed in claim 6, wherein the system comprises operation modes including:
    a first mode where the output of the at least one operational amplifier is connected to one of the plurality of passive circuit elements;
    a second mode where the output of the at least one operational amplifier is connected to another of the plurality of passive circuit elements; and
    a third mode where the output of the at least one operational amplifier is connected to two or more of the plurality of passive circuit elements.

9. A system as claimed in claim 8, wherein the third mode is temporarily operated when the system switches the first mode to the second mode.

10. A system as defined in claim 6, wherein a first passive circuit element of the plurality of passive circuit elements comprises a first resistor with a first resistor value, and wherein a second passive circuit element of the plurality of passive circuits comprises a second resistor with a second resistor value different from the first resistor value.

11. A system as defined in claim 1, wherein the system is for measuring a concentration of glucose.

12. A method for analyte measurement in use of a transimpedance amplifier, the transimpedance amplifier comprising at least one operational amplifier including a first input coupling to a reference voltage, a second input coupling to a sensor for sensing the analyte, and an output, and at least one passive circuit element having a first terminal and a second terminal, the first terminal of the at least one passive circuit element coupled to the second input of the at least one operational amplifier, the method comprising:
    monitoring a level of the output of the at least one operational amplifier during the measurement of the analyte; and
    adjusting a gain of the transimpedance amplifier for the measurement of the analyte in response to a gain adjustment circuit directly connected to the output of the at least one operational amplifier by changing the connection with the at least one passive circuit element without open-loop operation of the at least operational amplifier.

13. A method as defined in claim 12, comprising:
    repeating the step of measuring and the step of adjusting until the analyte measurement is completed.

14. A method as defined in claim 12, wherein the output of the at least one operational amplifier is coupled to an input for a controller for detecting and/or measuring the analyte level, the step of adjusting comprising:
connecting or disconnecting both of the output of the at least one operational amplifier and an input for a controller for detecting and/or measuring the analyte level, to or from the second terminal of the at least one passive circuit element.

15. A method as defined in claim 14, comprising:
detecting the analyte, using the at least one passive circuit element.

16. A method as defined in claim 12, wherein the at least one passive circuit element comprises a first passive circuit element and a second passive circuit element, the step of adjusting comprises:
selectively connecting at least one of the first passive circuit element and the second passive circuit element to the output of the at least one operational amplifier and an input for a controller for detecting and/or measuring the analyte level.

17. A method as defined in claim 16, wherein the step of connecting comprising:
connecting to one of the first passive circuit element or the second passive circuit element,
connecting to another one of the first passive circuit element or the second passive circuit element after connecting to both of the first passive circuit element or the second passive circuit element.

18. A method as defined in claim 16, wherein the first passive circuit comprises a first resistor with a first resistor value, and the second passive circuit comprises a second resistor with a second resistor value different from the first resistor value.

19. A method for measuring an analyte, comprising:
determining an output of an output of a transimpedance amplifier in response to the transimpedance amplifier being in a first configuration and a measurement of the analyte;
adjusting a gain of the transimpedance amplifier without the transimpedance amplifier operating in an open-loop in response to changing the configuration of the transimpedance amplifier to a second configuration; and
determining the output of the transimpedance amplifier in response to the transimpedance amplifier being in the second configuration.

20. The method of claim 19, wherein adjusting the gain of the transimpedance amplifier includes connecting or disconnecting an output of the transimpedance amplifier and an input for a controller for detecting and/or measuring the analyte level, to or from an input of the transimpedance amplifier.

* * * * *